(12) United States Patent
Romo-Nava

(10) Patent No.: US 10,857,356 B2
(45) Date of Patent: Dec. 8, 2020

(54) TRANSCUTANEOUS SPINAL CORD STIMULATION FOR TREATMENT OF PSYCHIATRIC DISORDERS

(71) Applicant: University of Cincinnati, Cincinnati, OH (US)

(72) Inventor: Francisco Romo-Nava, Mason, OH (US)

(73) Assignee: University of Cincinnati, Cincinnati, OH (US)

( * ) Notice: Subject to any disclaimer, the term of this patent is extended or adjusted under 35 U.S.C. 154(b) by 113 days.

(21) Appl. No.: 16/182,144

(22) Filed: Nov. 6, 2018

(65) Prior Publication Data

US 2019/0134386 A1    May 9, 2019

Related U.S. Application Data

(60) Provisional application No. 62/581,968, filed on Nov. 6, 2017.

(51) Int. Cl.
*A61N 1/20* (2006.01)
*A61N 1/36* (2006.01)
*A61N 1/04* (2006.01)

(52) U.S. Cl.
CPC .......... *A61N 1/20* (2013.01); *A61N 1/36025* (2013.01); *A61N 1/36034* (2017.08); *A61N 1/0456* (2013.01); *A61N 1/0492* (2013.01)

(58) Field of Classification Search
CPC ...... A61N 1/0456; A61N 1/0492; A61N 1/20; A61N 1/36025; A61N 1/36034
See application file for complete search history.

(56) References Cited

U.S. PATENT DOCUMENTS

| 2001/0003799 A1* | 6/2001 | Boveja | A61N 1/36017 607/45 |
| 2013/0138167 A1* | 5/2013 | Bradley | A61N 1/3605 607/5 |
| 2017/0312505 A1* | 11/2017 | Ahmed | A61F 7/08 |

OTHER PUBLICATIONS

Avery, Jason et al, Major depressive disorder is associated with abnormal interoceptive activity and functional connectivity in the insula; Biol Psychiatry, Aug. 1, 2014; 76(3): 258-266.
Bocci, Tommaso et al, Transcutaneous spinal direct current stimulation modulates human corticospinal system excitability; J Neurophysiol. Jul. 2015; 114(1): 440-446.
(Continued)

*Primary Examiner* — George Manuel
(74) *Attorney, Agent, or Firm* — Dinsmore & Shohl LLP

(57) ABSTRACT

Methods of treating a psychiatric disorder in a subject are provided which include placing at least one anode on an area of the subject's back over the dorsal spinal cord at the level of one or more of: thoracic vertebra 7 (T7), 8 (T8), 9 (T9), 10 (T10), 11 (T11), and 12 (T12) and lumbar vertebra 1 (L1); placing at least one cathode on an area of the subject's back which is generally rostral with reference to the anode; connecting the anode and the cathode to at least one source of direct and/or alternating electrical current; delivering direct current to the anode for a treatment period of time, the treatment period of time defining a tsDCS and/or tsACS treatment session, thereby modulating spinal input to the brain of the subject, decreasing sympathetic activity and reducing one or more symptoms and/or comorbidities associated with the psychiatric disorder.

18 Claims, 3 Drawing Sheets

(56) References Cited

OTHER PUBLICATIONS

Brunoni, Andre Russowsky et al, Heart rate variability is a trait marker of major depressive disorder: evidence from the sertraline vs. electric current therapy to treat depression clinical study; International Journal of Neuropsychopharmacology (2013) 16, 1937-1949.

Buijs, Ruud M., The autonomic nervous system: a balancing act; Handbook of Clinical Neurology, vol. 117, 3rd Series, Chapter 1, 2013.

Buis, Ruud M. et al, The circadian systema nd the balance of the autonomic nervous system; Handbook of Clinical Neurology, vol. 117, 3rd Series, Chapter 15, 2013.

Burchiel, Kim et al, Prospective, Multicenter Study of Spinal Cord Stimulation for Relief of Chronic Back and Extremity Pain; Spine, vol. 21, No. 23, 1996, pp. 2786-2794.

Cogiamanian, Filippo et al, Transcutaneous spinal cord direct current stimulation inhibits the lower limb nociceptive flexion reflex in human beings; Pain 152 (2011), 370-375.

Cogiamanian, Filippo et al, Transcutaneous spinal direct current stimulation; Frontiers in Psychicatry, Jul. 4, 2012.

Craig, A. D. (Bud), How do you feel—now? The anterior insula and human awareness; Neuroscience, vol. 10, Jan. 2009, 59-70.

Craig, A. D. (Bud), Significance of the insula for the evolution of human awareness of feelings from the body; Ann. N. Y. Acad. Sci. 1225 (2011) 72-82.

Deer, Timothy R. et al, The Appropriate Use of Neurostimulation of the Spinal Cord and Peripheral Nervous System for the Treatment of Chronic Pain and Ischemic Diseases: The Neuromodulation Appropriateness Consensus Committee; Neuromodulation 2014; 17: 515-550.

Deogaonkar, Milind et al, Spinal Cord Stimulation for the Treatment of Vascular Pathology; Neurosurg Clin N Am 25 (2014) 25-31.

Dongés, Siobhan et al, The effects of cervical transcutaneous spinal direct current stimulation on motor pathways supplying the upper limb of humans; PLOS ONE DOI: 10.1371/journal.poine.0172333, Feb. 22, 2017, 1-20.

Duerden, Emma G. et al, Lateralization of affective processing in the insula; NeuroImage 78 (2013) 159-175.

Gold PW, The organization of the stress system and its dysregulation in depressive illness; Molecular Psychiatry (2015) 20, 32-47.

Kumar, Krishna et al, The Effects of Spinal Cord Stimulation in Neuropathic Pain are Sustained: A 24-Month Follow-Up of the Prospective Randomized Controlled Multicenter Trial of the Effectiveness of Spinal Cord Stimulation; Neurosurgery 63: 2008, 762-770.

Liem, Liong et al, One-Year Outcomes of Spinal Cord Stimulation of the Dorsal Root Ganglion in the Treatment of Chronic Neuropathic Pain; Neuromodulation 2015; 18: 41-49.

Lim, Chai-Young and Shin, Hyung-Ik, Noninvasive DC stimulation on neck changes MEP; NeuroReport 2011, 22: 819-823.

Niérat, Marie-Cécile et al, Does Trans-Spinal Direct Current Stimulation Alter Phrenic Motoneurons and Respiratory Neuromechanical Outputs in Humans? A Double-Blind, Sham-Controlled, Randomized, Crossover Study; The Journal of Neuroscience, Oct. 22, 2014, 34(43): 14420-14429.

Owens, Matthew et al, Elevated morning cortisol is a stratified population-level biomarker for major depression in boys only with high depressive symptoms; PNAS, vol. 111, No. 9, Mar. 4, 2014, 3638-3643.

Parazzini, Marta et al, Modeling the current density generated by transcutaneous spinal direct current stimulation (tsCDS); Clinical Neurophysiology 125 (2014) 2260-2270.

Priori Alberto et al, Transcranial cerebellar direct current stimulation and transcutaneous spinal cord direct current stimulation as innovative tools for neuroscientists; J Physiol 592.16 (2014) 3345-3369.

De Oliveira Rocha, Roberto et al, Thoracic sympathetic block for the treatment of complex regional pain syndrome type I: A double-blind randomized controlled study; Pain 155 (2014) 2274-2281.

Schweizer, Lauren et al, Transcutaneous Spinal Direct Current Stimulation Alters Resting-State Functional Connectivity; Brain Connectivity, vol. 7, No. 6, 2017, 357-365.

Simmons, W. Kyle et al, Depression-related increases and decreases in appetite review dissociable patterns of aberrant activity in reward and interoceptive neurocircuitry; Am J Psychiatry, Apr. 1, 2016; 173(4): 418-428.

Simmons, W. Kyle et al, Keeping the Body in Mind: Insula Functional Organization and Functional Connectivity Integrate Interoceptive, Exteroceptive, and Emotional Awareness; Human Brain Mapping, 34: 3944-2958 (2013).

Sobocki, Jacek et al, Occipital C1-C2 Neuromodulation Decreases Body Mass and Fat Stores and Modifies Activity of the Autonomic Nervous System in Morbidly Obese Patients—A Pilot Study; Obes Surg (2013) 23: 693-697.

Truini, A. et al, Transcutaneous spinal direct current stimulation inhibits nociceptive spinal pathway conduction and increases pain tolerance in humans; European Journal of Pain 15 (2011) 1023-1027.

Wu Junfang et al, Spinal Cord Injury Causes Brain Inflammation Associated with Cognitive and Affective Changes: Role of Cell Cycle Pathways; The Journal of Neuroscience, Aug. 13, 2014; 34(33): 10989-11006.

\* cited by examiner

TRANSCUTANEOUS SPINAL CORD STIMULATION FOR TREATMENT OF PSYCHIATRIC DISORDERS

REFERENCE TO RELATED APPLICATION

This application claims priority from U.S. Provisional Patent Application Ser. No. 62/581,968, filed Nov. 6, 2017, the entire content of which is incorporated herein by reference.

FIELD OF THE INVENTION

The present invention relates generally to non-invasive methods of treating psychiatric disorders with electrical current delivered to the spine. The present invention relates specifically to transcutaneous methods of application of direct current or alternating current to the spinal cord for treating psychiatric disorders.

BACKGROUND OF THE INVENTION

Psychiatric disorders have long been recognized as particularly significant in that they severely affect functioning of afflicted individuals and few effective treatments are available.

Among psychiatric disorders, mood disorders are a significant concern, and major depressive disorder (MDD) is a highly prevalent and recurrent neuropsychiatric disorder that affects millions of people worldwide. In the United States, it is estimated that 14% of the population will suffer MDD during their lifetime. Psychiatric disorders represent a leading cause of years lived with disability worldwide and depressive disorders account for 40% of disability adjusted life years caused by mental disorders. MDD impairs ability to function and increases suffering, suicide risk, metabolic comorbidity, cardiovascular risk, morbidity/mortality and health care costs. Current treatment options for psychiatric disorders are only partially effective. For example, antidepressant medication effectiveness is variable and benefits only a portion of patients with small to moderate effect sizes and low response and remission rates. It is estimated that treatment with currently available antidepressants alleviates less than half the burden of MDD.

There is an urgent and unmet need for new and efficacious treatments for psychiatric disorders, particularly treatments for mood disorders, and even more particularly for treatment of depression.

SUMMARY OF THE INVENTION

A method of treating a psychiatric disorder in a subject is provided according to aspects of the present invention which includes: placing at least one anode on an area of the subject's back over the dorsal spinal cord at the level of one or more of: thoracic vertebra 7 (T7), 8 (T8), 9 (T9), 10 (T10), 11 (T11), and 12 (T12) and lumbar vertebra 1 (L1); placing at least one cathode on an area of the subject's body which is generally rostral with reference to the anode, such as on the back of the subject on or near a shoulder of the subject; connecting the anode and the cathode to at least one source of direct electrical current; delivering direct current to the anode for a treatment period of time, the treatment period of time defining a transcutaneous spinal direct current stimulation (tsDCS) treatment session, thereby modulating spinal input to the brain of the subject, decreasing sympathetic activity and reducing one or more symptoms and/or comorbidities associated with the psychiatric disorder.

According to aspects of a method of the present invention for treating a psychiatric disorder in a subject, the intensity of the direct current is in the range of 0.5 mA to 3 mA. According to aspects of a method of the present invention for treating a psychiatric disorder in a subject, the tsDCS treatment session has a duration the range of 1 minute to sixty minutes. According to aspects of a method of the present invention for treating a psychiatric disorder in a subject, a tsDCS treatment session is performed at least 1, 2, 3, 4, 5, 6, 7, 8, or more, or fewer, times per day. According to aspects of a method of the present invention for treating a psychiatric disorder in a subject, a tsDCS treatment session is performed at least 1, 2, 3, 4, 5, 6, 7, 8, or more, or fewer, times per week. According to aspects of a method of the present invention for treating a psychiatric disorder in a subject, the direct current has an average current density and the average current density is in the range from 1 mA/cm$^2$ to 25 mA/cm$^2$. According to aspects of a method of the present invention for treating a psychiatric disorder in a subject, both the anode and the cathode are in contact with the subject's skin and neither the anode nor the cathode is implanted in the subject. According to aspects of a method of the present invention for treating a psychiatric disorder in a subject methods of the present invention, the method further includes administering an additional therapeutic to treat the psychiatric disorder. According to aspects of a method of the present invention for treating a psychiatric disorder in a subject, the method further includes assessing at least one symptom, and/or at least one comorbid condition, associated with the psychiatric disorder before the tsDCS treatment session and assessing at least one symptom, and/or at least one comorbid condition, associated with the psychiatric disorder after the tsDCS treatment session. According to aspects of a method of the present invention for treating a psychiatric disorder in a subject, the at least one symptom is increased sympathetic tone. According to aspects of a method of the present invention for treating a psychiatric disorder in a subject, a conductive material is applied to one or more of: the at least one anode, the at least one cathode, skin of the subject, and two or more thereof.

A method of treating a mood disorder in a subject is provided according to aspects of the present invention which includes: placing at least one anode on an area of the subject's back over the dorsal spinal cord at the level of one or more of: thoracic vertebra 7 (T7), 8 (T8), 9 (T9), 10 (T10), 11 (T11), and 12 (T12) and lumbar vertebra 1 (L1); placing at least one cathode on an area of the subject's body which is generally rostral with reference to the anode, such as on the back of the subject on or near a shoulder of the subject; connecting the anode and the cathode to at least one source of direct electrical current; delivering direct current to the anode for a treatment period of time, the treatment period of time defining a transcutaneous spinal direct current stimulation (tsDCS) treatment session, thereby modulating spinal input to the brain of the subject, decreasing sympathetic activity and reducing one or more symptoms and/or comorbidities associated with the psychiatric disorder.

According to aspects of a method of the present invention for treating a mood disorder in a subject, the intensity of the direct current is in the range of 0.5 mA to 3 mA. According to aspects of a method of the present invention for treating a mood disorder in a subject, the tsDCS treatment session has a duration the range of 1 minute to sixty minutes. According to aspects of a method of the present invention for treating a mood disorder in a subject, the tsDCS treatment session is performed at least 1, 2, 3, 4, 5, 6, 7, 8 times, or more, or fewer, per day. According to aspects of a method of the present invention for treating a mood disorder in a subject, a tsDCS treatment session is performed at least 1, 2, 3, 4, 5, 6, 7, 8, or more, or fewer, times per week. According to aspects of a method of the present invention for treating a mood disorder in a subject, the direct current has an average current density and the average current density is in the range from 1 mA/cm$^2$ to 25 mA/cm$^2$. According to aspects of a method of the present invention for treating a mood disorder in a subject, both the anode and the cathode are in contact with the subject's skin and neither the anode nor the cathode is implanted in the subject. According to aspects of a method of the present invention for treating a mood disorder in a subject, methods of the present invention further include administering an additional therapeutic to treat the mood disorder. According to aspects of a method of the present invention for treating a mood disorder in a subject, methods of the present invention further include assessing at least one symptom, and/or at least one comorbid condition, associated with the mood disorder before the tsDCS treatment session and assessing at least one symptom, and/or at least one comorbid condition, associated with the mood disorder after the tsDCS treatment session. According to aspects of a method of the present invention for treating a mood disorder in a subject, the at least one symptom is increased sympathetic tone. According to aspects of a method of the present invention for treating a mood disorder in a subject, a conductive material is applied to one or more of: the at least one anode, the at least one cathode, skin of the subject, and two or more thereof.

A method of treating major depressive disorder in a subject is provided according to aspects of the present invention which includes: placing at least one anode on an area of the subject's back over the dorsal spinal cord at the level of one or more of: thoracic vertebra 7 (T7), 8 (T8), 9 (T9), 10 (T10), 11 (T11), and 12 (T12) and lumbar vertebra 1 (L1); placing at least one cathode on an area of the subject's body which is generally rostral with reference to the anode, such as on the back of the subject on or near a shoulder of the subject; connecting the anode and the cathode to at least one source of direct electrical current; delivering direct current to the anode for a treatment period of time, the treatment period of time defining a transcutaneous spinal direct current stimulation (tsDCS) treatment session, thereby modulating spinal input to the brain of the subject, decreasing sympathetic activity and reducing one or more symptoms and/or comorbidities associated with the major depressive disorder.

According to aspects of a method of treating major depressive disorder in a subject, the intensity of the direct current is in the range of 0.5 mA to 3 mA. According to aspects of a method of treating major depressive disorder in a subject, the tsDCS treatment session has a duration the range of 1 minute to sixty minutes. According to aspects of a method of treating major depressive disorder in a subject, the tsDCS treatment session is performed at least 1, 2, 3, 4, 5, 6, 7, 8, or more, or fewer, times per day. According to aspects of a method of treating major depressive disorder in a subject, a tsDCS treatment session is performed at least 1, 2, 3, 4, 5, 6, 7, 8, or more, or fewer, times per week. According to aspects of a method of treating major depressive disorder in a subject, the direct current has an average current density and the average current density is in the range from 1 mA/cm$^2$ to 25 mA/cm$^2$. According to aspects of a method of treating major depressive disorder in a subject, both the anode and the cathode are in contact with the subject's skin and neither the anode nor the cathode is implanted in the subject. According to aspects of a method of treating major depressive disorder in a subject, methods of the present invention further include administering an additional therapeutic to treat the major depressive disorder. According to aspects of a method of treating major depressive disorder in a subject, the additional therapeutic is: an antidepressant medication, psychotherapy, or a combination of an antidepressant medication and psychotherapy. According to aspects of a method of treating major depressive disorder in a subject, methods of the present invention further include assessing at least one symptom, and/or at least one comorbid condition, associated with the major depressive disorder before the tsDCS treatment session and assessing at least one symptom, and/or at least one comorbid condition, associated with the major depressive disorder after the tsDCS treatment session. According to aspects of a method of treating major depressive disorder in a subject, the at least one symptom is increased sympathetic tone. According to aspects of a method of treating major depressive disorder in a subject, a conductive material is applied to one or more of: the at least one anode, the at least one cathode, skin of the subject, and two or more thereof.

DETAILED DESCRIPTION OF THE INVENTION

Figure 1:
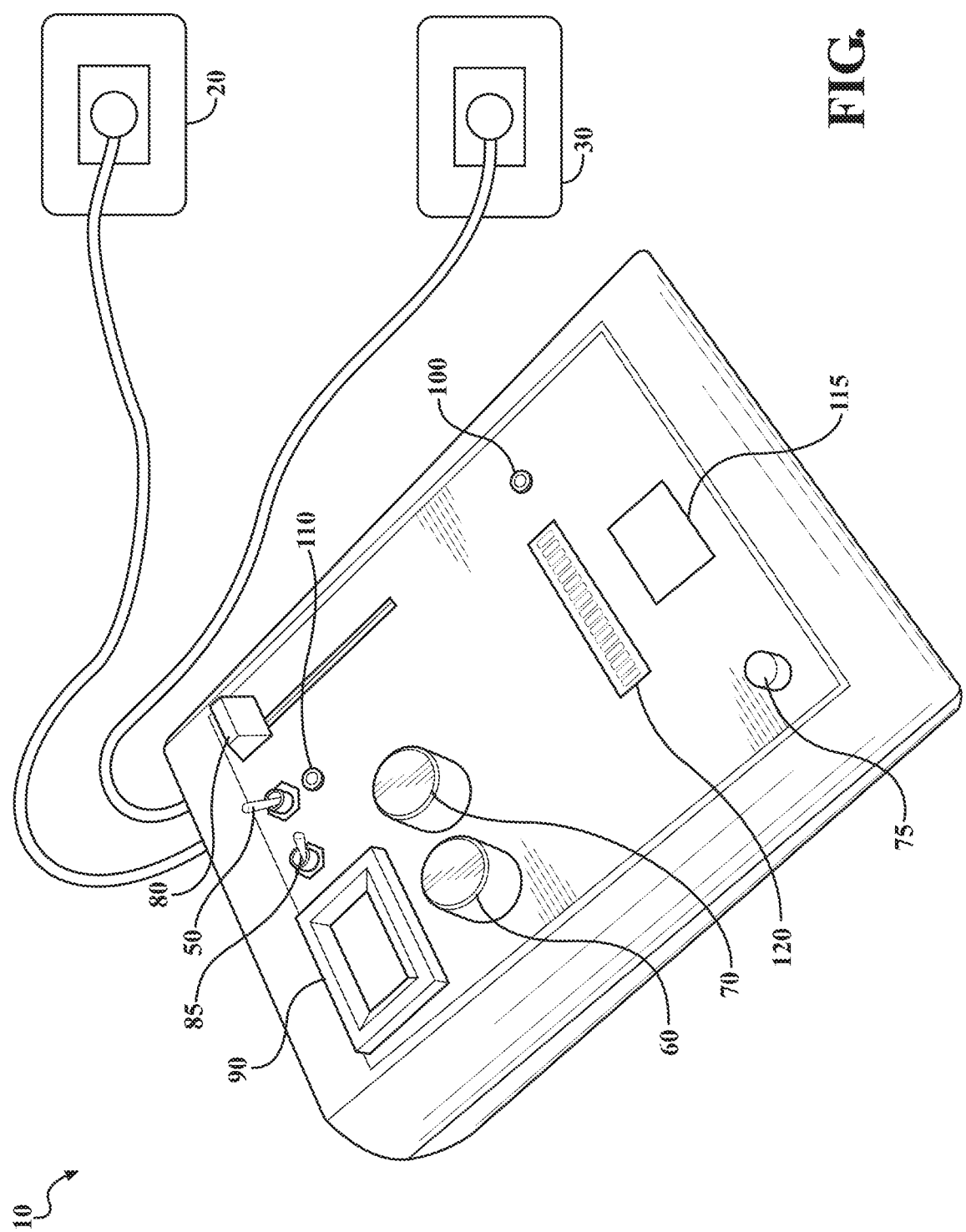
FIG. 1 is a schematic drawing of a tsDCS system.

The singular terms "a," "an," and "the" are not intended to be limiting and include plural referents unless explicitly stated otherwise or the context clearly indicates otherwise.

Methods are provided according to aspects of the present invention which modulate brain-body communication, thereby treating psychiatric disorders, such as mood disorders, including but not limited to, major depressive disorder (MDD).

Brain-body communication is believed to have an important role in the integration of mood and is therefore involved in mood disorders, including depression. Information travelling from the body to the brain through the dorsal horns in the spinal cord is essential to provide consciousness of emotional experience in a process called interoceptive awareness. This information is then used by the brain to adjust bodily function through hypothalamic and autonomic outputs. Increased sympathetic activity and somatic symptoms have been documented in MDD, indicative of disturbed brain-body communication.

Bi-directional brain-body communication is an essential component of emotional experience. The brain communicates with the body through neural and non-neural mechanisms that form a self-regulating circuit. For example, the hypothalamus is a complex neurological entity that represents just 0.3% (4 cm$^3$) of the adult human brain, but is a key region to understand brain output to the body. It controls systems essential in many physiological, endocrine and behavioral processes, including, among others, sleep/wake cycles, reproductive behavior, metabolic and cardiovascular regulation. These processes are tightly linked to higher cortical functions such as emotional regulation, fear responses, executive function, memory and pain and sensory perception that allow brain-body organization. The hypothalamus uses several pathways to communicate with the body through the outgoing hormonal and autonomic signals that need to be adequately synchronized in order to maintain homeostasis. Autonomic signals prepare the organs of the body for the coming hormones associated with the time of the day, moment for the reproduction cycle, feeding status and temperature. The hypothalamus not only modulates pre-autonomic neuronal systems connected to sympathetic and parasympathetic motor nuclei in brain stem and spinal cord, it also has hormonal 'motor' neurons able to release their content in the circulation. In addition, the hypothalamus receives information from the body about the level of metabolites and hormones, blood pressure and the physiological state of organs and is richly connected to the cortex. Via these elaborate pathways, the hypothalamus maintains a balance for optimal functioning of brain and body and deleterious consequences occur if this balance is lost or changed.

The communication between hypothalamus and body is bidirectional in order to maintain physiological balance. Somatic and sensory visceral information travels through the spinal dorsal horn (lamina I) and nucleus of the tractus solitarius (NTS), which convey spinal and parasympathetic information respectively to the thalamus. The thalamus sends the relevant information to cortical areas including the insula, providing consciousness of the corporal situation in a process called "interoceptive awareness." At this level, the organization of information appears to be asymmetrical, with parasympathetic fibers signaling the left posterior insula, and sympathetic fibers signaling the right posterior insula. Information next travels to the medial insula where the process of interoceptive awareness takes place and forms a cinemascopic version of emotional experience; this is essential for emotional processing and regulation as well as other cognitive processes such as motivational behavior and decision-making. The NTS information is also sent directly to the hypothalamus which acts accordingly to react or adapt bodily functions, and also sends and receives information to and from the prefrontal cortex. Light/dark cycles and food are among the biological signals that synchronize the brain and body physiology in activity periods and resting/digestion periods corresponding to day/night demands. The biological clock in the suprachiasmatic nucleus (SCN) of the hypothalamus signals the pre-autonomic neurons in the paraventricular nucleus (PVN) to adjust the physiology through the parasympathetic branch of the autonomic nervous system via the dorsal motor nucleus of the vagus (DMV) and the sympathetic branch through the intermediolateral column (IML) to target organs. Visceral and somatic information travels back to the brain through the vagus and nucleus of the tractus solitarius (NTS), the lamina I in the dorsal horn of the spinal cord to the thalamus and then to the right and/or left insula.

Another feedback mechanism between body and brain is through hormonal and humoral factors.

This complex neuronal crosstalk between body and brain is essential for emotions, fear responses, circadian organization, feeding and sexual behavior, blood pressure and temperature regulation, as well as energy metabolism.

Under physiological conditions, signaling from the body to the brain results in harmonious feedback to the hypothalamus and appropriate modulation of bodily functions via the autonomic nervous system and contribute to a euthymic mood. However, disturbed signaling from the body to the brain or from the brain to the body can alter physiology and influence mood.

Treatment Methods

According to aspects of methods of treatment of the present invention, psychiatric disorders, including mood disorders, are treated by non-invasively modulating spinal input to the brain, decreasing sympathetic activity, and restoring metabolic function as a consequence. In particular aspects of methods of treatment of the present invention, psychiatric disorders, including mood disorders, are treated by non-invasively modulating spinal input to the brain to produce a decrease in spinal input from the spinal cord to the brain (via the dorsal horn) and/or from brain sympathetic output to the body (via the intermediolateral column).

Modulation of spinal input to the brain according to aspects of methods of treatment of the present invention is accomplished by non-invasive spinal cord anodal stimulation by transcutaneous spinal direct current stimulation (tsDCS), transcutaneous spinal alternating current stimulation (tsACS), or a combination of both, at one or more of: thoracic vertebra 7 (T7), 8 (T8), 9 (T9), 10 (T10), 11 (T11), and 12 (T12) and lumbar vertebra 1 (L1), using a stimulation device, such as a tsDCS system or tsACS system, decreasing sympathetic activity and modulating spinal input to the brain, producing mood regulating effects, such as but not limited to, antidepressant effects; and/or improving other psychiatric symptoms, including but not limited to, anxiety, somatic symptoms, autonomic symptoms, and dissociative symptoms. Outcome of treatment by modulation of spinal input to the brain using anodal tsDCS and/or tsACS can be assessed by one or more of: psychometric instruments, measures of mood disorder symptom severity, anxiety, somatic symptoms of mood disorders, interoceptive awareness, autonomic function, and metabolic markers known to be regulated by sympathetic activity. Changes in interoceptive awareness, somatic symptoms, autonomic and metabolic parameters resulting from tsDCS and/or tsACS methods of the present invention are associated with changes in mood disorder symptom severity, such as MDD symptom severity. Thus, anodal tsDCS and/or tsACS treatment of a subject having a psychiatric disorder according to methods of the present invention will produce beneficial results including one or more of: a decrease in depressive symptom sub-components, a beneficial change in interoceptive awareness, a decrease in anxiety, a decrease in sympathetic tone, a decrease in somatic symptoms, beneficial change in autonomic parameters, and beneficial change in metabolic parameters. According to aspects, anodal tsDCS and/or tsACS treatment of a subject having a mood disorder according to methods of the present invention will produce beneficial results including one or more of: a decrease in depressive symptom sub-components, a beneficial change in interoceptive awareness, a decrease in anxiety, a decrease in sympathetic tone, a decrease in somatic symptoms, beneficial change in autonomic parameters, and beneficial change in metabolic parameters. According to aspects, anodal tsDCS and/or tsACS treatment of a subject having major depressive disorder according to methods of the present invention will produce beneficial results including one or more of: a decrease in depressive symptom sub-components, a beneficial change in interoceptive awareness, a decrease in anxiety, a decrease in sympathetic tone, a decrease in somatic symptoms, beneficial change in autonomic parameters, and beneficial change in metabolic parameters.

Methods of treatment according to aspects of the present invention treat a psychiatric disorder, including but not limited to a mood disorder, by non-invasively modulating spinal input to the brain using anodal tsDCS and/or tsACS without significant effect on motor functions. Methods of treatment according to aspects of the present invention treat MDD by non-invasively modulating spinal input to the brain using anodal tsDCS and/or tsACS without significant effect on motor functions.

A method of treating a psychiatric disorder in a subject according to aspects of the present invention include: placing at least one anode on an area of the subject's back over the dorsal spinal cord at the level of one or more of: thoracic vertebra 7 (T7), 8 (T8), 9 (T9), 10 (T10), 11 (T11), and 12 (T12) and lumbar vertebra 1 (L1); placing at least one cathode on an area of the subject's body which is generally rostral with reference to the anode, such as on the back of the subject on or near a shoulder of the subject; connecting the anode and the cathode to at least one source of direct electrical current; delivering direct current to the anode, thereby modulating spinal input to the brain of the subject by anodal spinal stimulation, decreasing sympathetic activity and reducing one or more symptoms and/or comorbidities associated with the psychiatric disorder. The cathode is placed at a position on the subject which is generally rostral with reference to the anode and can be ventral and rostral with reference to the anode, e.g. on the upper abdomen, chest, front or side of the neck or head according to aspects of the present invention. The cathode is placed at a position on the subject which is generally rostral with reference to the anode and can be on the back, shoulder, back of the neck or head according to aspects of the present invention. According to aspects, the psychiatric disorder to be treated is a mood disorder. According to aspects, the psychiatric disorder to be treated is major depressive disorder.

The intensity of the direct current is generally in the range of 0.5 mA to 3 mA, but can be higher or lower. According to aspects of methods of treating a psychiatric disorder in a subject of the present invention, the intensity of the direct current is in the range of 1.5 mA to 2.5 mA. According to aspects of methods of treating a psychiatric disorder in a subject of the present invention, the intensity of the direct current is in the range of 1.8 mA to 2.2 mA, such as 2.0 mA.

According to aspects of methods of treating a psychiatric disorder in a subject of the present invention, the direct current has an average current density and the average current density is in the range from 1 $mA/cm^2$ to 25 $mA/cm^2$.

The direct current is delivered to the subject via anodal stimulation for a duration of 1 minute to sixty minutes, the duration defining a tsDCS treatment session. According to aspects of methods of treating a psychiatric disorder in a subject of the present invention, a tsDCS treatment session has a duration of 5 minutes to 30 minutes. According to aspects of methods of treating a psychiatric disorder in a subject of the present invention, a tsDCS treatment session has a duration of 10 minutes to 20 minutes.

A method of treating a psychiatric disorder in a subject according to aspects of the present invention include: placing at least one anode on an area of the subject's back over the dorsal spinal cord at the level of one or more of: thoracic vertebra 7 (T7), 8 (T8), 9 (T9), 10 (T10), 11 (T11), and 12 (T12) and lumbar vertebra 1 (L1); placing at least one cathode on an area of the subject's body which is generally rostral with reference to the anode, such as on the back of the subject on or near a shoulder of the subject; connecting the anode and the cathode to at least one source of direct electrical current; delivering alternating current to the anode, thereby modulating spinal input to the brain of the subject by anodal spinal stimulation, decreasing sympathetic activity and reducing one or more symptoms and/or comorbidities associated with the psychiatric disorder. The cathode is placed at a position on the subject which is generally rostral with reference to the anode and can be ventral and rostral with reference to the anode, e.g. on the upper abdomen, chest, front or side of the neck or head according to aspects of the present invention. The cathode is placed at a position on the subject which is generally rostral with reference to the anode and can be on the back, shoulder, back of the neck or head according to aspects of the present invention. According to aspects, the psychiatric disorder to be treated is a mood disorder. According to aspects, the psychiatric disorder to be treated is major depressive disorder.

The intensity of the alternating current is generally in the range of 0.5 mA to 3 mA, but can be higher or lower. According to aspects of methods of treating a psychiatric disorder in a subject of the present invention, the intensity of the alternating current is in the range of 1.5 mA to 2.5 mA. According to aspects of methods of treating a psychiatric disorder in a subject of the present invention, the intensity of the alternating current is in the range of 1.8 mA to 2.2 mA, such as 2.0 mA.

According to aspects of methods of treating a psychiatric disorder in a subject of the present invention, the alternating current has an average current density and the average current density is in the range from 1 $mA/cm^2$ to 25 $mA/cm^2$.

The alternating current is delivered to the subject via anodal stimulation for a duration of 1 minute to sixty minutes, the duration defining a tsACS treatment session. According to aspects of methods of treating a psychiatric disorder in a subject of the present invention, a tsACS treatment session has a duration of 5 minutes to 30 minutes. According to aspects of methods of treating a psychiatric disorder in a subject of the present invention, a tsACS alternating current source has a frequency in the range of 2 Hz to 50 Hz.

According to aspects of methods of treating a psychiatric disorder in a subject of the present invention, tsACS stimulation.

According to aspects of methods of treating a psychiatric disorder in a subject of the present invention, a tsDCS and/or tsACS treatment session is performed at least 1, 2, 3, 4, 5, 6, 7, 8, or more, or fewer, times per week.

According to aspects of methods of treating a psychiatric disorder in a subject of the present invention, a tsDCS and/or tsACS treatment session is performed at least 1, 2, 3, 4, 5, 6, 7, 8, or more, or fewer, times per day.

According to aspects of methods of treating a psychiatric disorder in a subject of the present invention, a tsDCS and/or tsACS treatment session is performed at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more, or fewer, times per month.

The terms "subject" and "patient" interchangeably refer herein to an individual in need of treatment of a psychiatric disorder. While the present invention describes methods for treatment of human subjects in need thereof, the present invention is not limited to human subjects and the term subject generally includes mammals and birds, such as, but not limited to, non-human primates, cats, dogs, cows, horses, rodents, pigs, sheep, goats and poultry.

A therapeutically effective protocol for tsDCS and/or tsACS treatment of a psychiatric disorder will vary depending on the severity of the condition to be treated, the age and sex of the subject and the general physical characteristics of the subject to be treated. Further, the treatment may be adjusted depending on whether treatment is to be acute or continuing. One of skill in the art could determine a therapeutically effective amount in view of these and other considerations typical in medical practice.

Psychiatric Disorders

Psychiatric disorders treated according to methods of the present invention include mood disorders, attention-deficit hyperactivity disorder (ADHD), along with non-psychiatric comorbidities of psychiatric disorders. Subjects are identified as having a psychiatric disorder using well-known medical and diagnostic techniques.

The term "mood disorder" refers to major depressive disorder (MDD), bipolar disorder, and anxiety disorders. The term "anxiety disorders" refers to generalized anxiety, panic disorder, post-traumatic stress syndrome, obsessive-compulsive disorder, and phobias. Altered sensory input to the brain through the dorsal horns of the spinal cord contributes to the pathophysiology of symptoms of mood disorders, such as depressive symptoms. Without wishing to be bound by theory, mood can be viewed as the subjective experience that results from the integration of corporeal sensory input travelling through the spinal cord (lamina I) and the vagus nerve which convey spinal and parasympathetic information, respectively to the nucleus of the tractus solitarius (NTS) in the brainstem. This information is then relayed to the thalamus and finally to the insula, where it is interpreted in a process called interoceptive awareness. This process allows human awareness of homeostasis and a cinemascopic version of emotional experience. Thus, interoceptive awareness is an essential part of mood and seems to play an important role in mood disorders, including, but not limited to, MDD.

The brain uses the information gathered from the body to adjust corporeal function through hypothalamic and autonomic outputs. During a depressive episode, patients experience autonomic dysregulation suggesting that the sensory input to the brain might be disturbed and play a role in the pathogenesis of mood disorders, including, but not limited to, MDD. Specifically, increased sympathetic tone is associated with depression.

MDD is often recurrent and/or chronic and is strongly associated with stress, circadian rhythm disruption and other environmental and genetic factors. MDD is characterized by a cluster of symptoms that include not only a low, sad or irritable mood, but also decreased attention and motivation, self-defeating and suicidal thoughts, and disturbance of other cognitive domains, sleep, appetite and sexual interest. Additionally, anxiety, pain and other somatic complaints are present in more than half of patients diagnosed with MDD.

MDD is characterized by disturbed autonomic nervous system function. The stress response system involving the hypothalamic-pituitary-adrenal axis and the sympatho-medullary system is hyperactive before, during and after depressive episodes (see Gold P W., Mol Psychiatry. 2015; 20(1): 32-47). Evidence of such hyperactivity can be observed in the form of increased cortisol (see Owens M, et al., Proc Natl Acad Sci USA. 2014; 111(9):3638-43) and leptin (see Milaneschi Y, et al., Biol Psychiatry, 2015), as well as decreased adiponectin (see Li L, et al., J Diabetes Metab. 2016; 7(4)) levels in patients with MDD. Cortisol, adiponectin, leptin and fibroblast growth factor-21 (FGF-21) levels are a reflection of the autonomic output from the brain to the body; particularly sympathetic tone (see Bornstein S R, et al., J Clin Endocrinol Metab. 1999; 84(5):1729-36), which is also regulated by the biological clock located in the suprachiasmatic nucleus of the hypothalamus (see Buijs R M., Handb Clin Neurol. 2013; 117:1-11; Bookout A L, et al., Nat Med. 2013; 19(9):1147-52; Shea S A, et al., J Clin Endocrinol Metab. 2005; 90(5):2537-44; Lilley T R, et al., Endocrinology. 2012; 153(2):732-8). LCn-3 fatty acids also play an important role in brain-body communication and are involved in regulating circadian, and autonomic function (see Lavialle M et al., J Nutr. 2008; 138(9):1719-24; and Mozaffarian D, et al., Circulation. 2008; 117(9):1130-7). LCn-3 have been implicated in the pathophysiology and antidepressant treatment response of MDD (see McNamara R K. et al., J Nutr Intermed Metab. 2016; 5:96-106). The metabolic hormone FGF-21, which is mainly produced by the liver, is an important signal for biological clock regulation (see Bookout A L, et al., Nat Med. 2013; 19(9):1147-52) and it is largely driven by sympathetic tone (see Douris N, et al., Endocrinology. 2015; 156(7):2470-81).

Circadian cortisol release by the adrenal gland greatly depends on sympathetic tone under the control of the biological clock and not entirely on ACTH release (see Lilley T R, et al., Endocrinology. 2012; 153(2):732-8). This could help explain why the dexamethasone suppression test failed as a diagnostic tool and as a reliable predictor of treatment response for MDD patients (see Ribeiro S C, et al., Am J Psychiatry. 1993; 150(10:1618-29). Increased cortisol level in MDD is often interpreted as a cause of MDD (see Herbert J., Psychol Med. 2013; 43(3):449-69), but instead could be a consequence of other phenomenon such as a disturbed brain-body communication, such as increased sympathetic tone. Increased sympathetic activity has also been documented in MDD patients in the form of decreased heart rate variability (see Brunoni A R, et al., Int J Neuropsychopharmacol. 2013; 16(9):1937-49; and Kemp A H, et al., PLoS One. 2012; 7(2):e30777), which is inversely correlated with depressive symptom severity (see Yeh T C, et al., Prog Neuropsychopharmacol Biol Psychiatry. 2016; 64:60-7; and Wang Y, et al., BMC Psychiatry. 2013; 13:187). MDD patients show increased comorbidity with obesity (see Gibson-Smith D, et al., J Clin Psychiatry. 2016; 77(2):e144-51), metabolic syndrome (see Vancampfort D, et al., Psychol Med. 2014; 44(10):2017-28) and diabetes (see Chen S, et al., Endocrine. 2016; 53(1):35-46), all of which are associated with increased sympathetic tone (see Kreier F, et al., Diabetes. 2003; 52(11):2652-6). Taken together, this evidence suggests an important role of the autonomic nervous system and disturbed brain-body communication in the pathophysiology of MDD that could also explain the increased cardiovascular risk of this disorder (see Goldstein B I, et al., Circulation. 2015; 132(10):965-86; and Shi S, et al., Psychosom Med. 2017; 79(2):153-61). It further suggests the possibility that levels of metabolic markers such as cortisol, adiponectin, leptin, and FGF-21 are disturbed during MDD as a consequence of increased sympathetic activity.

ADHD is a psychiatric disorder characterized by an ongoing pattern in inattentive behavior and/or hyperactivity-impulsivity that interferes with functioning and/or development.

Non-psychiatric comorbidities of psychiatric disorders, include, for depression: metabolic syndrome, obesity, diabetes, cardiovascular risk and other comorbidities related to increased sympathetic tone.

Combination Treatments

According to aspects of the present invention, combination therapies can be used which include: (1) administration of tsDCS and/or tsACS according to a method of the present invention; and (2) administration of one or more additional therapeutics to treat a psychiatric disorder in a subject. The additional therapeutic(s) may be administered during a course of treatment at the same time as the tsDCS and/or tsACS, at a different time than the tsDCS and/or tsACS, prior to the tsDCS and/or tsACS, subsequent to the tsDCS and/or tsACS, or a combination of any thereof.

Combination treatments can allow for reduced time of a course of treatment, reduced dosage of administered treatments, and increased therapeutic index compared to treatment with a single treatment type.

Additional therapeutics for treatment of a psychiatric disorder include, but are not limited to, medications such as antidepressant medications, mood stabilizing medications (e.g. for bipolar disorders), stimulants (e.g. for ADHD); psychotherapy; an invasive neuromodulation tool, such as an implanted electrode(s) in electrical connection to a stimulation source, and non-invasive neuromodulation tools. Invasive neuromodulation tools, such as an implanted electrode(s) in electrical connection to a stimulation source, include, but are not limited to, vagal stimulation, deep brain stimulation, or a combination thereof. Non-invasive neuromodulation tools include, but are not limited to, transcranial direct current stimulation, transcranial magnetic stimulation, transcutaneous vagal stimulation, and a combination of any two or more thereof.

Antidepressant medications that can be administered include, but are not limited to, tricyclic antidepressants, tetracyclic antidepressants, selective serotonin reuptake inhibitors, monoamine oxidase inhibitors, norepinephrine reuptake inhibitors, norepinephrine-dopamine reuptake inhibitors, and serotonin-norepinephrine reuptake inhibitors.

Monoamine oxidase inhibitors useful as antidepressants include, but are not limited to, bifemelane, isocarboxazid, moclobemide, nialamide, phenelzine, pirlindole, toloxatone, and tranylcypromine.

Tricyclic antidepressants useful as antidepressants include, but are not limited to, amineptine, amitriptyline, amitriptylinoxide, amoxapine, clomipramine, desipramine, dibenzepin, dosulepin, doxepin, imipramine, lofepramine, maprotiline, melitracen, nitroxazepine, nortriptyline, noxiptiline, opipramol, pipofezine, protriptyline, tianeptine, and trimipramine.

Tetracyclic antidepressants useful as antidepressants include, but are not limited to, maprotiline, mianserin, mirtazapine, and setiptiline.

Selective serotonin reuptake inhibitors useful as antidepressants include, but are not limited to, citalopram, escitalopram, fluoxetine, fluvoxamine, paroxetine, and sertraline.

Norepinephrine reuptake inhibitors useful as antidepressants include, but are not limited to, atomoxetine, bupropion, ciclazindol, esreboxetine, maprotiline, radafaxine, reboxetine, talopram, tandamine, teniloxazine, and viloxazine.

Norepinephrine-dopamine reuptake inhibitors useful as antidepressants include, but are not limited to, bupropion.

Serotonin-norepinephrine reuptake inhibitors useful as antidepressants include, but are not limited to, desvenlafaxine, duloxetine, levomilnacipran, milnacipran, and venlafaxine.

Mood stabilizing medications include, but are not limited to, carbamazepine, divalproex sodium, lamotrigine, lithium, and valproic acid.

Stimulants useful in treatment of, for example, ADHD, include, but are not limited to, amphetamine, dextroamphetamine, dexmethylphendiate, methylphenidate, and lisdexamfetamine.

A therapeutically effective amount of such medications will vary depending on the particular pharmaceutical composition used, the severity of the condition to be treated, the age and sex of the subject and the general physical characteristics of the subject to be treated. Further, dosage may be adjusted depending on whether treatment is to be acute or continuing. One of skill in the art could determine a therapeutically effective amount in view of these and other considerations typical in medical practice.

The term "course of treatment" refers to a period of time over which a subject is treated for a psychiatric condition. In general, a course of treatment extends days, months, or years, until the desired beneficial effect is achieved, e.g. amelioration of signs or symptoms of the psychiatric disorder.

tsDCS and/or tsACS System

A tsDCS and/or tsACS system includes at least one anode, at least one cathode, and various controls included in a stimulator/control unit. FIG. 1 is a schematic drawing of a tsDCS and/or tsACS system 10 including an anode (20), a cathode (30), and various controls included in a stimulator/control unit, such as, but not limited to, controls for: 1) powering the device on (50), modulating current (60), modulating duration (70), timing the duration of the treatment (75), modulating intensity (80), and quick "abort" switch (85). Various display elements may be included, such as a timer display (90), a low battery indicator (100), a light indicating power is on (110), a current level display (115) and an indicator of the quality of contact of the electrode with the skin of the subject (120). A power supply powers the tsDCS and/or tsACS system such as a battery, which can be a disposable or rechargeable battery, such as, without limitation, a 9-volt battery; an alternating current source (such as a wall socket source of AC), an alternating current source in combination with an AC-to-DC converter; or other suitable power source. For anodal stimulation, the active electrode is the anode and the reference electrode is the cathode. During stimulation, current flows between the electrodes, passing through the spinal cord in a generally caudal-to-rostral direction (also described as distal to proximal direction) to complete the circuit.

Figure 2:
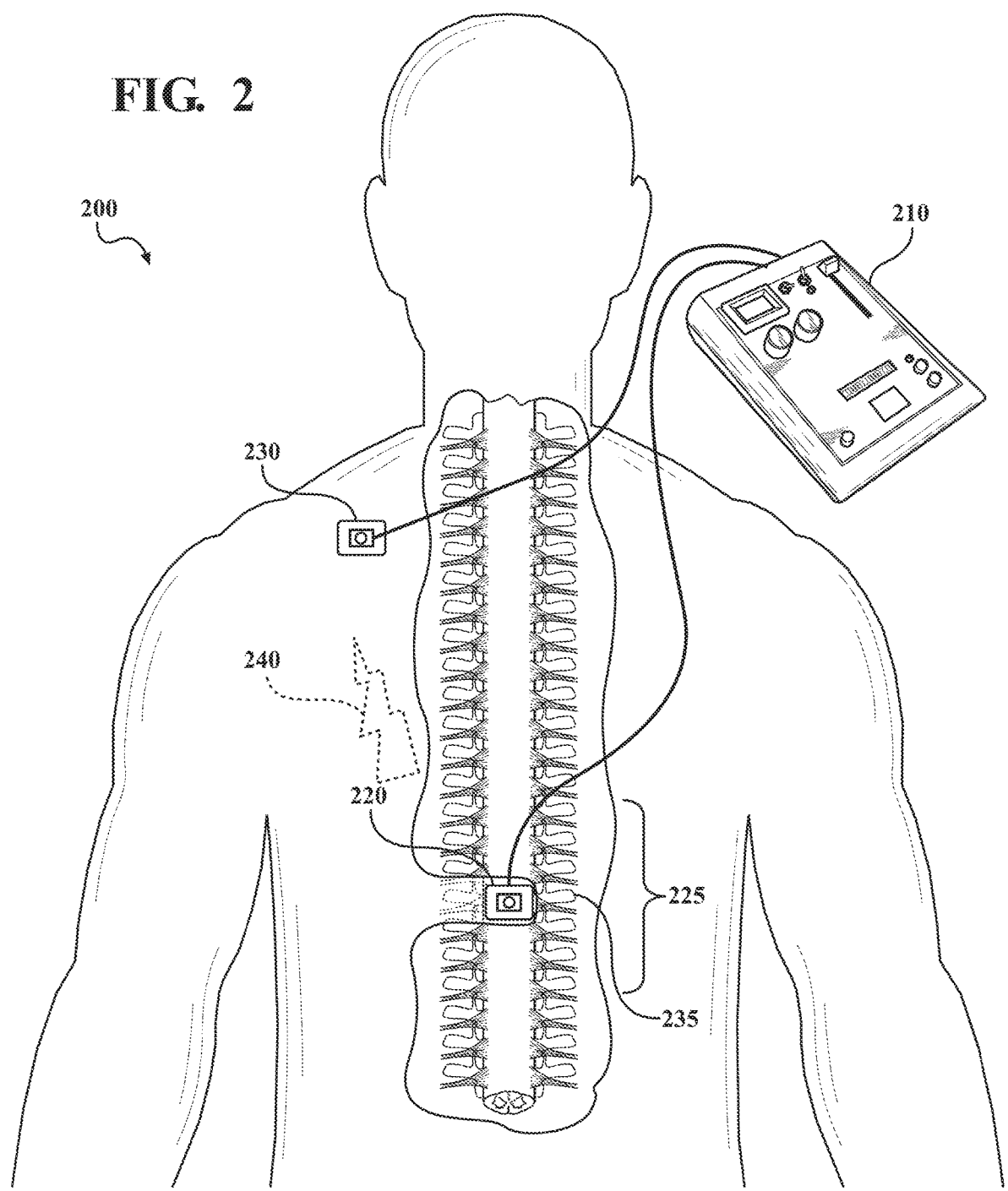
FIG. 2 is a schematic drawing showing treatment of a subject with tsDCS.

FIG. 2 is a schematic drawing showing treatment of a subject with tsDCS and/or tsACS, 200. In FIG. 2, a tsDCS and/or tsACS anodal stimulator/control unit 210 is in electrical connection with an anode (220) and a cathode (230), wherein the anode is in electrical conductive contact with the skin of the subject's back at the level of the $10^{th}$ thoracic vertebra (235) of the spinal cord (245) and the cathode is in electrical conductive contact with the skin of the subject's back near the shoulder. Bracket 225 shows the region of thoracic vertebra 7 (T7), 8 (T8), 9 (T9), 10 (T10), 11 (T11), and 12 (T12) and lumbar vertebra 1 (L1). The symbol (240) diagrammatically illustrates that the tsDCS and/or tsACS system is functioning.

Anodes and cathodes used can have any of a variety of shapes and sizes. Commonly used electrodes have a surface area in the range of about 9 $cm^2$ to 75 $cm^2$, such as 5 cm×5 cm, 5 cm×7 cm, or 5 cm×10 cm, but these may be larger or smaller. In general, the ratio of the total surface area of the anode(s) to the total surface area of the cathode(s) is in the range of 2:1 to 1:2, such as in the range of 1.5:1 to 1:1.5, such as in the range of 1.4:1 to 1:1.4, such as in the range of 1:1.2 to 1.2:1, or such as 1:1, although this ratio may be greater or smaller. Anodes and cathodes can be made of any suitable material, such as, but not limited to, rubber, cloth, polymeric materials, and combinations of such materials.

A tsDCS and/or tsACS system may be obtained commercially or may be constructed from commercially available components.

The anode(s) and cathode(s) of the tsDCS and/or tsACS system are placed in contact with the skin of the subject non-invasively, i.e. the anode(s) and cathode(s) are not implanted in the body of the subject and do not break, or pass through, the skin of the subject. A conductive material may be applied to the anode(s), cathode(s), and/or skin of the subject to enhance conductivity, such as, but not limited to, saline, conductive paste, or conductive gel (such as EEG paste, electrolyte gel). Typically, the conductive material is skin compatible so as not to cause undue irritation or discomfort.

Electrodes are optionally secured to the skin. For example, a physical securing mechanism such as an elastic band, a cloth wrapping, or adherent overlay can be applied; and/or a chemical securing mechanism such as a skin-compatible adhesive can be used.

Figure 3:
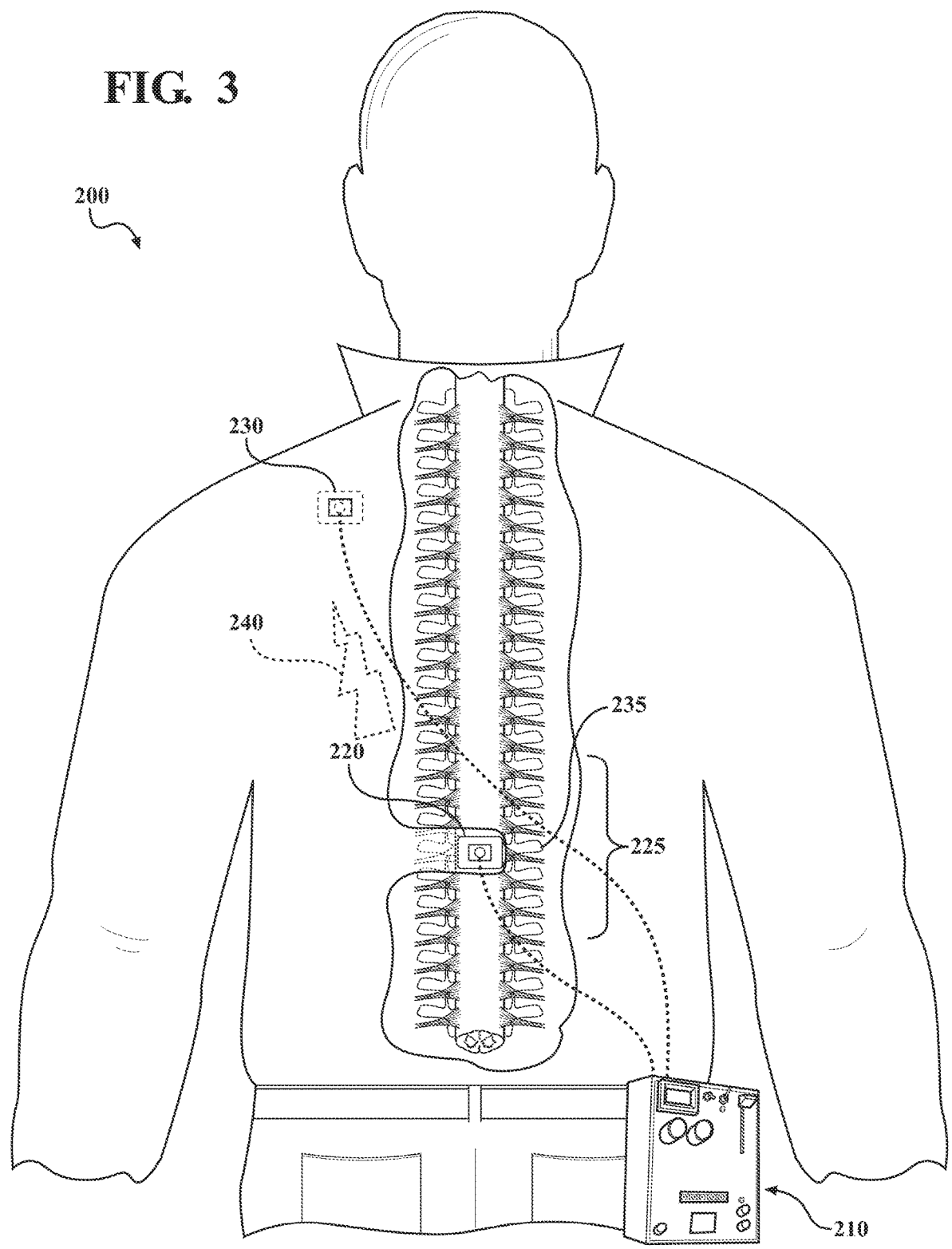
FIG. 3 is a schematic drawing showing treatment of a subject with tsDCS while the subject is clothed, highlighting the portability of the tsDCS system and convenience of the treatment method.

The tsDCS and/or tsACS system is portable such that the subject optionally can wear the tsDCS and/or tsACS system while moving about and engaging in daily activities. FIG. 3 is a schematic drawing showing treatment of a subject with tsDCS and/or tsACS, 200, as in FIG. 2. The subject is wearing clothing and carries the easily portable tsDCS device attached to a belt in this illustration. In FIG. 3, a tsDCS and/or tsACS stimulator/control unit 210 is in electrical connection with an anode (220) and a cathode (230), wherein the anode is in electrical conductive contact with the skin of the subject's back at the level of the $10^{th}$ thoracic vertebra (235) of the spinal cord (245) and the cathode is in electrical conductive contact with the skin of the subject's back near the shoulder. Bracket 225 shows the region of thoracic vertebra 7 (T7), 8 (T8), 9 (T9), 10 (T10), 11 (T11), and 12 (T12) and lumbar vertebra 1 (L1). The symbol (240) diagrammatically illustrates that the tsDCS and/or tsACS system is functioning.

Embodiments of inventive compositions and methods are illustrated in the following examples. These examples are provided for illustrative purposes and are not considered limitations on the scope of inventive compositions and methods.

EXAMPLES

An 8-week, double blinded, randomized, sham controlled, parallel group, clinical trial study was designed in which a total of 20 adult antidepressant-free MDD patients will be randomized to receive Active (n=10) or Sham (n=10) tsDCS protocols for 8 weeks in a 1:1 ratio.

Outcome of treatment by modulation of spinal input to the brain using tsDCS will be assessed by one or more of: psychometric instruments, measures of mood disorder symptom severity, anxiety, somatic symptoms of mood disorders, interoceptive awareness, autonomic function, and metabolic markers known to be regulated by sympathetic activity. The study combines the use of a tsDCS system for stimulation treatment, with one or more methods of assessing the effectiveness of the stimulation treatment: psychometric instruments to diagnose MDD (M.I.N.I.), measures of depressive symptom severity (MADRS and PHQ-9), assessment of somatic symptoms (4DSQ), assessment of interoceptive awareness (MAIA), assessment of autonomic function (blood pressure, heart rate), and assessment of metabolic markers (cortisol, LCn-3 fatty acids, adiponectin, leptin, insulin and fibroblast growth factor-21) known to be regulated by sympathetic activity.

Overview

Inclusion criteria: 1) age 18-50 yrs., inclusive; 2) female or male; 3) BMI 18.5 to 30 kg/mts$^2$, inclusive; 4) current MDD episode diagnoses confirmed by Mini International Neuropsychiatric Interview (MINI) 5.0 with a duration of ≥1 month and ≤24 months; 5) moderate MDD symptoms according to Montgomery-Asberg Depression Rating Scale (MADRS) score ≥20 to ≤35; 6) no current or recent (past month) antidepressant pharmacological treatment; 7) GAD and other anxiety symptoms are not permitted; 8) using an effective contraceptive method (all participants of childbearing potential).

Exclusion criteria: 1) Current or lifetime MDD episode non-responsive to two or more antidepressant treatments at adequate doses and time (including ECT); 2) Current or lifetime bipolar disorder diagnosis, comorbid PTSD, psychotic or substance use disorder (nicotine and caffeine allowed); 3) current use of cannabis; 4) significant risk of suicide according to CSSRS or clinical judgment, or suicidal behavior in the past year: 5) current chronic pain conditions; 6) current chronic use of opioids, medications that affect blood pressure, other analgesics or drugs with significant autonomic effects; 7) neurological, endocrinological, cardiovascular (including diagnosed hypertension) or other clinically significant medical conditions as judged by the clinician; 8) skin lesions on electrode placement region; 9) implanted electrical medical devices; 10) Pregnancy; 11) suspected IQ<80, and 12) any other clinically relevant reason as judged by the clinician.

The Mini International Neuropsychiatric Interview 5.0 (MINI, described in Sheehan D V, et al., 1998; 59 Suppl 20:22-33; quiz 4-57) is being used to confirm the diagnosis of current MDD and evaluate the presence of comorbid psychiatric disorders. The Montgomery-Asberg Depression Rating Scale (MADRS, described in Montgomery S A, et al., Br J Psychiatry. 1979; 134:382-9) is being used to evaluate depressive symptom severity and the Columbia Suicide Severity Rating Scale (CSSRS, described in Posner K, et al., Am J Psychiatry. 2011; 168(12):1266-77) is being used to evaluate suicidality. The clinical global impression-severity (CGI-S) and the clinical global impression-improvement (CGI-I, described in Busner J, et al., Psychiatry (Edgmont). 2007; 4(7):28-37) scales are being used to evaluate the overall clinical severity and improvement of the illness. Participants also complete self-report instruments including the Patient Health Questionnaire-9 (PHQ-9, described in Kroenke K, et al., J Gen Intern Med. 2001; 16(9):606-13) as an additional measure of depressive symptom severity. The Four-Dimensional Symptom Questionnaire (4DSQ, described in Terluin B, et al., BMC Psychiatry. 2006; 6:34) is being used to measure distress, somatization and anxiety symptoms, the Binge Eating Scale (BES, described in Gormally J, et al., Addict Behav. 1982; 7(1): 47-55) is being used to measure eating behaviors and aspects of body perception and the multidimensional assessment of interoceptive awareness (MAIA, described in Mehling W E, et al., PLoS One. 2012; 7(11):e48230) is being used as a quantitative measure of interoceptive awareness.

tsDCS Device and Use Parameters

The 2×2 Soterix® Medical transcutaneous spinal direct current stimulator model 0707-A device is being used. This device provides anodal stimulation delivered at 2.5 mA per 20-minute session or sham session consisting of short pulses (of the desired intensity) at the beginning and end of the sessions. If stimulation intensity (in active or sham protocols) is not tolerable at 2.5 mA, the clinician may decide to decrease intensity to 2.0 mA or 1.5 mA. If subject has tolerated a stimulation intensity of less than 2.5 mA, the study clinician may increase the dose to 2.0 mA or 2.5 mA when considered clinically appropriate. An anode electrode (5×10 cm) is placed at the level of the T10 vertebral spinal process. At this level, the current is expected to spread longitudinally through the spinal cord up to three additional vertebral levels. The cathode (5×7 cm) electrode is placed on the right shoulder over the deltoid area. Participants will be scheduled to receive sham or active tsDCS sessions three times/week.

Blood and Urine Samples

General: Blood samples (approximately 20 ml per occasion) are obtained on visit 0 and 6 for a) Hematology: Complete blood count (CBC); b) electrolytes; c) liver panel; d) kidney panel; e) lipid panel; f) other: glucose and TSH. A urine sample for urinalysis will be collected at screening. A serum human chorionic gonadotrophin (HCG) determination (blood pregnancy test) will be conducted at visit 0, visit 4 and 6 (if applicable).

Special focus metabolic markers: A blood sample (approximately 5 ml per occasion) is obtained on visit 1, 4 and 6 for: adiponectin, leptin, cortisol, insulin and FGF-21 levels. A blood sample (approximately 5 ml per occasion) is obtained for Fatty acid analyses: Patients (N=20) have their blood fatty acid composition determined by gas chromatography at visit 1, visit 4, and visit 6.

Cardiovascular Measurements

Blood pressure is obtained before and after tsDCS sessions through the auscultatory technique using a standard mercury sphygmomanometer in a sitting position after 5 minutes of rest. An ECG tracing is obtained through standard 12-lead electrocardiography at visit 0, 1, 4, and 6. For the purpose of this study, blood pressure and heart rate are considered as variables to assess cardiovascular autonomic function.

Anthropometric Measures

Height is obtained at screening. Weight, waist circumference, abdominal circumference and Body Mass Index (BMI) are measured on visits 0, 1, 3, 4, 5 and 6.

Protocol Visits—See Also Table I

Visit 0 (Screening)

Clinical staff evaluate the participant (subject) in order to obtain a psychiatric and medical history. The MINI is used to confirm MDD diagnosis, the MADRS to evaluate depressive symptom severity and the CSSRS for suicidality. A full neurological and physical evaluation, ECG, cardiovascular measurements, laboratory tests, urinalysis, urine drug test, and a blood pregnancy test (if applicable) are performed. After eligibility is confirmed, a baseline visit is scheduled.

Visit 1 (Baseline). After verification of eligibility, subjects are randomized to an "active" or to a "sham" tsDCS protocol. Treatment allocation remains double-blinded throughout the study to raters and study physicians. A MADRS, CGI-S, CSSRS, PHQ-9, 4DSQ, BES and MAIA will be completed for each subject. BMI, waist circumference, abdominal circumference, vital signs, blood sample and ECG will be obtained for each subject.

tsDCS sessions (1-24): Three tsDCS sessions per week will be scheduled for each subject. A CSSRS is completed before each tsDCS session. Blood pressure and heart rate are evaluated prior and after each tsDCS session for each subject. Adverse events (AEs) are assessed after each session through open-ended questions.

Full visits 2, 3, 4, and 5: A MADRS, CSSRS, CGI-S, CGI-I, PHQ-9, 4DSQ, BES and MAIA scales will be completed for each subject. Anthropometric measures (Visit 4), vital signs, and ECG will be obtained for each subject. A blood sample (visit 4), urine drug test (Visit 4) and pregnancy test will be performed if applicable (visit 4). AEs will be recorded after each tsDCS session.

Full Visit 6 (Final visit): A MADRS, CSSRS, CGI-S, CGI-I, PHQ-9, 4DSQ, BES and MAIA scales will be completed for each subject. Anthropometric measures, vital signs, blood sample, pregnancy test and ECG will be obtained for each subject. AEs will be recorded after each tsDCS session.

Primary Outcome Assessment: Difference in change from baseline to week 8 (or last available observation) in MADRS scores between active and sham tsDCS groups.

Secondary Outcome Assessment: a) differences in AE's frequency between active and sham tsDCS groups, b) association between change from baseline to week 8 (or last available observation) in MADRS scores, and clinical (CGI-I, CGI-S, PHQ-9, MAIA, BES and 4DSQ), autonomic (BP, HR) and metabolic (anthropometric, adiponectin, leptin, cortisol, FGF-21 and LCn-3) parameter change from baseline to week 8 (or last available observation), and c) MADRS sub-component (94) scores, clinical parameters (CGI-I, CGI-S, PHQ-9, MAIA, BES and 4DSQ), autonomic (BP, HR), and metabolic (anthropometric, adiponectin, leptin, cortisol, insulin FGF-21 and LCn-3) parameters change from baseline to week 8 (or last available observation) difference between Active and Sham tsDCS groups.

Data Analysis.

Efficacy: longitudinal effect of tsDCS will be assessed by comparing change in MADRS scores from baseline to week 8 (or last available observation). To take maximum advantage of intermediate observations while avoiding assumptions about the trajectory of change over time, a repeated-measures ANOVA model (i.e., with time as a categorical variable) will be used.

Safety: a similar analysis as used for efficacy data will be performed for laboratory assays, vital signs, anthropometric, clinical, autonomic and metabolic variables. Frequencies of AE's will be compared between groups using comparative analysis.

Evaluation of association of baseline and change in interoceptive awareness, somatic symptoms, clinical, autonomic and metabolic parameters with change in depressive symptom severity: a correlation analysis will be used to evaluate the association between treatment and depressive symptom severity, both total and in components (items). Correlation analysis will also be performed by gender, autonomic and metabolic parameters.

Analysis of the effect of active tsDCS treatment on interoceptive awareness, anxiety and somatic symptoms, clinical, autonomic and metabolic parameters: longitudinal effect of tsDCS will be assessed by comparing MADRS sub-component scores, clinical parameters (CGI-I, CGI-S, PHQ-9, BES, MAIA, and 4DSQ), autonomic, and metabolic parameters change from baseline to week 8 (or last available observation) difference between Active and Sham groups using a repeated-measures ANOVA as described above. Throughout, tests and confidence intervals for effect sizes will be two-sided, $\alpha=0.05$.

TABLE I

Schedule of events

| | Screen Visit 0 (Day -14 +/- 7) | Baseline Visit 1 (Day 0) | Visit 2 Day 7 +/- 4 | Visit 3 (Day 14 +/- 4) | Visit 4 (Day 28 +/- 4) | Visit 5 (Day 46 +/- 4) | Final Visit Visit 6 (Day 56 +/- 4) |
|---|---|---|---|---|---|---|---|
| MINI | X | | | | | | |
| MADRS | X | X | X | X | X | X | X |
| PHQ-9, | | X | X | X | X | X | X |
| CGI-S & CGI-I, 4DSQ, BES and MAIA. | | X | X | X | X | X | X |
| CBC, LFT, Renal, Lipid, Glucose and TSH. | X | | | | | | X |
| Urinalysis | X | | | | | | X |
| Serum HCG | X | X | | | X | | X |
| Drug Urine test. | X | | | | X | | X |
| Adiponectin, FGF-21, Leptin, LCn-3, Insulin, Cortisol | | X | | | X | | X |
| Anthropometric measurements | X | X | | | X | | X |
| EKG | X | X | | | X | | X |
| Physical and Neurological Evaluation | X | X | | X | X | | X |

| | Screen | Baseline | Week 1 | Week 2 | Week 3 | Week 4 | Week 5 | Week 6 | Week 7 | Final Visit |
|---|---|---|---|---|---|---|---|---|---|---|
| tsDCS sessions | | X | X X X | X X X | X X X | X X X | X X X | X X X | X X X | X |
| CSSRS | X | X | X X X | X X X | X X X | X X X | X X X | X X X | X X X | X |
| Blood Pressure*, HR* | | X | X X X | X X X | X X X | X X X | X X X | X X X | X X X | X |
| Adverse Events | | X | X X X | X X X | X X X | X X X | X X X | X X X | X X X | X |

Complete Blood Count (CBC);
Liver Function Test (LFT);
Thyroid stimulating hormone (TSH);
Fibroblast Growth Factor-21 (FGF-21),
Long Chain fatty acids (LCn-3),
Heart Rate (HR),
Electrocardiogram (EKG),
*Measured pre and post tsDCS session.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of treating a psychiatric disorder in a subject, comprising:
    placing at least one anode on an area of the subject's back over the dorsal spinal cord at the level of one or more of: thoracic vertebra 7 (T7), 8 (T8), 9 (T9), 10 (T10), 11 (T11), and 12 (T12) and lumbar vertebra 1 (L1);
    placing at least one cathode on an area of the subject's back which is generally rostral with reference to the anode;
    connecting the anode and the cathode to at least one source of direct electrical current;
    delivering direct current to the anode for a treatment period of time, the treatment period of time defining a transcutaneous spinal direct current stimulation (tsDCS) treatment session, thereby modulating spinal input to the brain of the subject, decreasing sympathetic activity and reducing one or more symptoms and/or comorbidities associated with the psychiatric disorder; and
    wherein both the anode and the cathode are in contact with the subject's skin and neither the anode nor the cathode is implanted in the subject.

2. The method of claim 1, wherein the psychiatric disorder is a mood disorder.

3. The method of claim 2, wherein the mood disorder is major depressive disorder.

4. The method of claim 1, wherein the intensity of the direct current is in the range of 0.5 mA to 3 mA.

5. The method of claim 1, wherein the tsDCS treatment session has a duration the range of 1 minute to sixty minutes.

6. The method of claim 5, wherein a tsDCS treatment session is performed at least 1, 2, 3, 4, 5, 6, 7, or 8 times per day.

7. The method of claim 5, wherein a tsDCS treatment session is performed at least 1, 2, 3, 4, 5, 6, 7, or 8 times per week.

8. The method of claim 1, wherein the direct current has an average current density and the average current density is in the range from 1 mA/cm$^2$ to 25 mA/cm$^2$.

9. The method of claim 1, further comprising administering an additional therapeutic to treat the psychiatric disorder.

10. The method of claim 9, wherein the psychiatric disorder is major depressive disorder and the additional therapeutic is an antidepressant medication.

11. The method of claim 9, wherein the psychiatric disorder is major depressive disorder and the additional therapeutic is psychotherapy.

12. The method of claim 1, further comprising assessing at least one symptom associated with the psychiatric disorder before the tsDCS treatment session and assessing at least one symptom associated with the psychiatric disorder after the tsDCS treatment session.

13. The method of claim 12, wherein the at least one symptom is increased sympathetic tone.

14. The method of claim 1, wherein a conductive material is applied to one or more of: the at least one anode, the at least one cathode, skin of the subject, and two or more thereof.

15. A method of treating major depressive disorder in a subject, comprising:
   placing at least one anode on an area of the subject's back over the dorsal spinal cord at the level of one or more of: thoracic vertebra 7 (T7), 8 (T8), 9 (T9), 10 (T10), 11 (T11), and 12 (T12) and lumbar vertebra 1 (L1);
   placing at least one cathode on an area of the subject's back which is generally rostral with reference to the anode;
   connecting the anode and the cathode to at least one source of direct electrical current;
   delivering direct current to the anode for a treatment period of time, the treatment period of time defining a transcutaneous spinal direct current stimulation (tsDCS) treatment session, thereby modulating spinal input to the brain of the subject, decreasing sympathetic activity and reducing one or more symptoms and/or comorbidities associated with the major depressive disorder; and
   wherein both the anode and the cathode are in contact with the subject's skin and neither the anode nor the cathode is implanted in the subject.

16. The method of claim 15, wherein the intensity of the direct current is in the range of 0.5 mA to 3 mA.

17. The method of claim 15, wherein the tsDCS treatment session has a duration the range of 1 minute to sixty minutes.

18. The method of claim 15, wherein the direct current has an average current density and the average current density is in the range from 1 mA/cm$^2$ to 25 mA/cm$^2$.

* * * * *